US012758410B2

(12) United States Patent
Sima

(10) Patent No.: US 12,758,410 B2
(45) Date of Patent: Oct. 13, 2026

(54) ORTHOPEDIC JOINT DEVICE

(71) Applicant: OTTO BOCK HEALTHCARE PRODUCTS GMBH, Vienna (AT)

(72) Inventor: Harald Sima, Herzogenburg (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 1136 days.

(21) Appl. No.: 17/774,823

(22) PCT Filed: Nov. 6, 2020

(86) PCT No.: PCT/EP2020/081294
§ 371 (c)(1),
(2) Date: May 5, 2022

(87) PCT Pub. No.: WO2021/094219
PCT Pub. Date: May 20, 2021

(65) Prior Publication Data

US 2022/0401244 A1 Dec. 22, 2022

(30) Foreign Application Priority Data

Nov. 11, 2019 (DE) ..................... 10 2019 130 326.5

(51) Int. Cl.
*F04B 1/324* (2020.01)
*A61F 2/64* (2006.01)
(Continued)

(52) U.S. Cl.
CPC .................. *A61F 5/01* (2013.01); *A61F 2/64* (2013.01); *A61F 2/74* (2021.08); *F04B 1/324* (2013.01); *F04B 1/124* (2013.01)

(58) Field of Classification Search
CPC ........ A61F 2/64; A61F 2/74; A61F 2002/643; A61F 2002/6845; A61F 2/70;
(Continued)

(56) References Cited

U.S. PATENT DOCUMENTS 3,883,900 A 5/1975 Jerard et al.
6,764,520 B2 7/2004 Deffenbaugh et al.
(Continued)

FOREIGN PATENT DOCUMENTS

DE 3703759 A1 * 9/1987 ........... F16H 37/021
DE 601 12 403 T2 6/2006
(Continued)

OTHER PUBLICATIONS

Translation of International Search Report (Year: 2021).*
(Continued)

*Primary Examiner* — Christie Bahena
(74) *Attorney, Agent, or Firm* — HOLLAND & HART LLP

(57) ABSTRACT

An orthopedic joint device is provided, the device having an upper part, a lower part pivotably mounted thereon and an actuator fastened to the upper part and the lower part and having a drive shaft coupled to an output element via a force transmission device, the force transmission device having a load transmission element that can by adjusted depending on the load.

19 Claims, 4 Drawing Sheets

(51) Int. Cl.

| | |
|---|---|
| ***A61F 2/74*** | (2006.01) |
| ***A61F 5/01*** | (2006.01) |
| *F04B 1/124* | (2020.01) |

(58) Field of Classification Search

CPC .. A61F 2002/6436; B25J 9/0006; F16H 9/00; F16H 9/08; F16H 7/14; F04B 1/324

See application file for complete search history.

(56) References Cited

U.S. PATENT DOCUMENTS

| | | | | |
|---|---|---|---|---|
| 8,257,446 | B2 | 9/2012 | Puchhammer | |
| 9,091,309 | B2 | 7/2015 | Battlogg | |
| 2006/0249315 | A1* | 11/2006 | Herr | A61F 2/6607 623/47 |
| 2013/0150980 | A1* | 6/2013 | Swift | A61F 2/70 623/24 |
| 2018/0098864 | A1 | 4/2018 | Auberger et al. | |
| 2019/0231562 | A1 | 8/2019 | Pusch et al. | |

FOREIGN PATENT DOCUMENTS

| | | | | |
|---|---|---|---|---|
| DE | 10 2006 006 966 | A1 | 8/2007 | |
| DE | 10 2010 055 833 | A1 | 3/2012 | |
| DE | 102016221718 | A1 * | 5/2017 | F16H 7/18 |
| DE | 102016118999 | B4 * | 5/2018 | A61F 2/70 |
| EP | 3522836 | A1 | 8/2019 | |
| JP | S62251476 | | 2/1987 | |
| WO | WO-2010005473 | A1 * | 1/2010 | A61F 2/70 |
| WO | WO-2014007917 | A1 * | 1/2014 | A61F 2/644 |
| WO | 2018/065570 | A1 | 4/2018 | |

OTHER PUBLICATIONS

Translation of DE102016118999B4 (Year: 2016).*

Translation of DE102016221718A1 (Year: 2016).*

Translation of DE3703759A1 (Year: 1987).*

"International Search Report and Written Opinion of the International Searching Authority," issued in connection with Int'l Appl. No. PCT/EP2020/081294, dated Feb. 19, 2021 (14 pages).

* cited by examiner

ORTHOPEDIC JOINT DEVICE

CROSS REFERENCE TO RELATED APPLICATIONS

This is a national phase application of International Application No. PCT/EP2020/081294, filed 6 Nov. 2020, which claims the benefit of German Patent Application No. 10 2019 130 326.5, filed 11 Nov. 2019, the disclosures of which are incorporated herein, in their entireties, by this reference.

TECHNICAL FIELD

The invention relates to an orthopedic joint device having an upper part, a lower part pivotably disposed thereon, and an actuator which is fastened to the upper part and lower part and which comprises a driveshaft coupled to a driven element by way of a force transmission device. In particular, the orthopedic joint device is in the form of a prosthesis or orthosis.

BACKGROUND

Prostheses serve to replace missing or lost extremities, and often comprise a joint device for an articulated interconnection between two prosthesis components. The movement of the two prosthesis components in relation to one another can be influenced by damper devices, this case relating to passive prosthetic joint devices. A corresponding statement applies to orthoses which are applied to extremities present. In this case, too, joint devices interconnect two components in articulated fashion. A relative movement between the two components is actively caused or assisted when an orthopedic joint device is provided with an actuator. To this end, at least one drive is provided, the latter being coupled to a source of power such that the movement behavior can be actively influenced. The actuator may comprise an electric motor which is used to move further components of the actuator, for example parts of a hydraulic pump or a transmission device.

Hydraulic pumps, especially hydraulic pumps in orthopedic devices, are driven by a motor, especially by an electric motor. The motors need to be comparatively small and light, and the motor or motors is or are optionally coupled to the remaining components of the hydraulic pump by way of a transmission. When designing the hydraulic pump and the entire so-called drivetrain, it is necessary to define a work point for the motor when the construction starts. The work point defines the rotational speed and an optimal torque which allows the motor to operate optimally, for example have the best efficiency. In relation to the hydraulic pump, this means that the pump has an appropriate flow rate at this work point or conveys a certain volumetric flow rate and builds up appropriate pressure. Should the desired pressure and volumetric flow rate not be able to be obtained by direct connection between motor and driveshaft, it is necessary to provide a required gear reduction by way of an interposed transmission, depending on work point and drive. The work range of a drivetrain then emerges from the characteristic of the motor and the chosen gear reduction of the transmission.

Very high forces and torques act on orthopedic joint devices. At the same time, there is little installation space available and there are restrictions in relation to the weight. Therefore, small, fast-running electric motors are used as drives for orthopedic devices, and these are coupled to transmissions in order to apply the desired forces and torques.

Electric motors with permanent magnets, what are known as permanent magnet-excited or external magnet-excited electric motors, have a comparatively stiff characteristic, that is to say in comparison with other motor technologies the rotational speed only drops slightly in the case of an increased load. Such a behavior is desirable for many applications. Specifically for applications in the field of prostheses and orthoses, it would sometimes be advantageous to be able to adapt the characteristic of the drivetrain to the respective application without efficiency losses or without substantial efficiency losses.

A correspondingly high rotational speed of the motor with a correspondingly low torque is desired when a hydraulic actuator assists a patient with walking in the plane, for example within the scope of prosthetic or orthotic care, and this corresponds to a high flow rate at a comparatively low pressure. However, should there be increased assistance, for example when walking uphill, climbing stairs or getting up, it is high forces, and hence high pressures, at a comparatively low flow rate that are required, rendering a low rotational speed necessary. It is not possible to cover both work points, or only difficult to cover both work points, in the case of a drivetrain defined once from a structural point of view with a fixed transmission ratio or gear reduction. A further limitation here is also given by the maximum current of the power storage device, for example a rechargeable battery, which is directly proportional to the motor torque. The size of the power storage device is limited, especially also for reasons of space and weight. Hence, an increase in the gear reduction would be required to obtain higher torques.

Upper extremity prostheses use change gears that facilitate two work points. Load-dependent clutches that require a complex structure are provided to this end. Moreover, the switching steps are defined, and so an adjustment, advantageously a continuous adjustment, to different load situations is not possible.

SUMMARY

It is an object of the present invention to provide an orthopedic device that renders an increase in the work range of drivetrains possible.

According to the invention, this object is achieved by an orthopedic joint device having the features of the main claim. Advantageous embodiments and developments of the invention are disclosed in the dependent claims, the description and the drawings.

The orthopedic joint device having an upper part, a lower part pivotably disposed thereon, and an actuator which is fastened to the upper part and lower part and which comprises a driveshaft coupled to a driven element by way of a force transmission device provides for the force transmission device to comprise a load-dependently adjustable force transmission element. In order to cause an automatic load-dependent adjustment of the force transmission element, the latter is preferably mounted in elastically prestressed fashion. If there is a change in the load, and hence resistance, on the force transmission element, the force transmission element adjusts automatically and causes a change in the transmission ratio or in the force transmission, for example a change in a piston stroke. By changing the position of the force transmission element, it is possible to alter the characteristic of the drive or type of drive and automatically load-dependently adapt these to the respective conditions. In the case of an increasing resistance, for example pressure or torque, there is a change in the position of the force transmission element; by way of example, there is a change in the piston stroke or in the position and transmission ratio of a transmission such that lower pressures or lower forces or torques are provided.

In an embodiment of the invention, the orthopedic joint device comprises a hydraulic pump which has a housing and which is assigned a drive, in particular an electric motor. The electric motor is coupled to the driveshaft and may be disposed within the housing of the hydraulic pump or fastened to the housing of the hydraulic pump. Should the motor be activated and rotate the driveshaft, the driven element in the form of a displacement element is displaced, for example rotated or axially displaced in the case of an axial piston pump. The adjustable force transmission element is disposed between the driveshaft and the displacement element, which sucks the hydraulic fluid into the pump chamber and then ejects it from the latter again. To cause a load-dependent automatic adjustment of the force transmission element, the latter is preferably mounted in elastically prestressed fashion. If there is a change in the load, that is to say in the resistance on the force transmission element as a result of the displacement element, there is an automatic adjustment of the force transmission element, and this causes a change in the stroke of the at least one displacement element. The volumetric flow rate of the pump can be influenced by changing the stroke. The position of the force transmission element changes when the pressure increases; by way of example, the piston stroke changes as a result of a change in the inclination of a swash plate or changes as a result of a change in the eccentricity of a cam such that the effective stroke of the displacement element is decreased in the case of increasing pressure and the volumetric flow rate drops.

A development of the invention provides for the displacement element to be in the form of a piston of an axial piston pump and for the force transmission element to be in the form of a swash plate. The swash plate may be mounted on a carrier in elastically prestressed or resilient fashion such that there is a load-dependent change in the inclination of the swash plate depending on the pressure exerted by the piston or pistons on the force transmission element or on the swash plate. A further variant of the invention provides for the displacement element to be in the form of a piston of a radial piston pump, with the force transmission element then being in the form of a cam. The load-dependently changeable cam eccentricity can be obtained by way of a shaft cam, for example, which can rotate in relation to a second cam. An effective summated eccentricity arises depending on the relative angle position between the two cams and said summated eccentricity load-dependently changes on account of the elastic mount of the cams with respect to one another. Furthermore, it is possible for the displacement element to be in the form of a rotor of a sliding vane rotary pump and for the force transmission element to be in the form of a cam. The eccentricity in this case may also be altered by rotating two cams relative to one another, with the rotation being implemented load-dependently, preferably against a prestressing force.

To be able to bring about the load-dependent change in the stroke of the at least one displacement element, at least one spring element which is compressed when the load increases is advantageously disposed between the driveshaft and the displacement element. The displacement element need not be disposed directly on the driveshaft; instead, it is possible for a carrier or a support to be disposed on the driveshaft, with the carrier element being elastically mounted on said carrier or on said support. One or more spring elements which is or are compressed when the load increases may be disposed on the displacement element. The spring element or the spring elements may be interchangeably disposed on the displacement element in order to facilitate an adjustment of the change behavior of the displacement element. A harder spring element is used if the change in the stroke should be implemented over a relatively large force range or resistance range, while a softer spring element is chosen if there should be a stroke change with a faster response. A different maximum stroke can be defined by way of interchangeable spring elements in order to be able to specify structurally different limits.

The spring element may be in the form of an elastomeric spring, coil spring, spiral coil spring, Belleville spring, Belleville spring assembly and/or leaf spring. It is possible to use different types of spring elements together; it is likewise possible to use differently hard or soft spring elements of the same type or of different types in order to achieve the desired change behavior.

A development of the invention provides for the force transmission device to be in the form of a continuously variable, adjustable transmission, for example as a friction gear with conical rollers rolling against one another or a belt transmission or friction drive, in which axially displaceable pulley pairs are disposed on two substantially parallel shafts. If the pulleys of a pair are moved toward one another, a belt or a rolling element migrates outward since there is a change in the diameter of the area of contact. The other pulley pair is correspondingly moved apart such that the effective diameter of the area of contact reduces there. This allows the attainment of a continuously variable, load-dependent change in the transmission ratio between driveshaft and driven shaft.

The force transmission element can be in the form of a conical pulley which is part of the force transmission device. The force transmission element is formed on the driveshaft or a driven shaft so as to be displaceable along the latter's longitudinal extent, for example displaceably mounted on a splined shaft or mounted on a thread so as to be rotatable relative to the respective shaft, and prestressed against a rotation. The prestress can be produced by way of a spring element which is coupled to the conical pulley. The spring, for example a torsional spring, is stressed if a greater drive torque is transmitted, as a result of which a relative rotation sets in between the shaft and the conical pulley. If two conical pulleys are present, both can in the case of an adjustment be moved away from one another or toward one another simultaneously as a result of opposing threads. The movement is reversed if the transmitted drive torque is reduced. By way of example, the force is transmitted between the driveshaft and the driven shaft by way of rolling elements, one or more belts or chains, especially in correspondingly constructed conical pulley pairs. The two conical pulley pairs may be directly coupled to one another by way of levers or guide rods such that a separating movement of the one conical pulley pair brings about a converging movement of the other conical pulley pair, and vice versa.

The respective spring element may have a linear, degressive or progressive spring characteristic in order to be able to optimally adjust the conveying characteristic of the hydraulic pump to the respective demands.

The orthopedic joint device is provided in particular for the use in prostheses, orthoses and, as a special case thereof, exoskeletons. In principle, it is also possible to assemble the actuator of the hydraulic pump, optionally with an integrated motor or a motor securely coupled therewith and with an energy storage device, to other orthopedic devices, for example wheelchairs, joint movers or the like.

BRIEF DESCRIPTION OF THE DRAWINGS

Exemplary embodiments of the invention are explained in more detail below on the basis of the attached drawings, in which.

DETAILED DESCRIPTION

Figure 1:
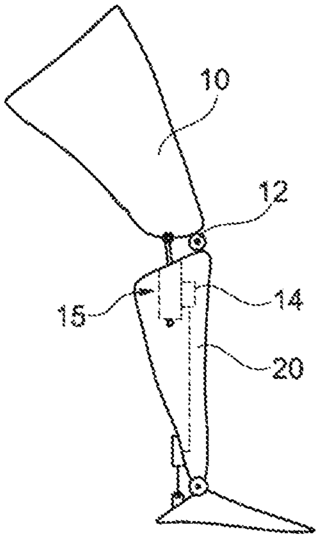
FIG. 1 shows a schematic representation of a joint device.

FIG. 1 shows a schematic representation of an orthopedic joint device in the form of a prosthesis of a lower extremity, having an upper part 10 and a lower part 20 which are mounted on one another in articulated fashion about a pivot axis 12. In the exemplary embodiment illustrated, the upper part 10 has a prosthetic shaft which serves to receive an above-knee stump. Other orthopedic devices, such as upper extremity prostheses and upper or lower extremity orthoses should likewise be considered to be orthopedic joint devices if the components thereof are mounted on one another in articulated fashion. An actuator 15 is disposed between the upper part 10 and the lower part 20. In the illustrated exemplary embodiment, the actuator 15 is in the form of a linear-action actuator 15 and comprises a drive 14 in the form of an electric motor for the purposes of bringing about an adjustment in the position of the upper part 10 relative to the lower part 20. By way of example, the actuator 15 can be in the form of a hydraulic-action actuator and may comprise a pump that is driven by the drive 14. A hydraulic fluid is pumped via the pump into a pump chamber or into a chamber closed off by a piston. The piston is coupled to a piston rod, which is mounted on the upper part 10 or the lower part 20. By appropriately pumping the hydraulic fluid into the pump chamber, the piston rod is moved in one direction or the other, and the upper part 10 is pivoted relative to the lower part 20. As a result, an extension movement or a flexion movement of the joint device can be implemented, braked or assisted. As an alternative to a hydraulic embodiment of the actuator 15, the latter may also have a mechanical form such that a spindle, for example, is driven by way of the drive 14. The spindle may then enter or leave an actuator housing in order to bring about an extension or flexion of the orthopedic joint device.

Figure 2:
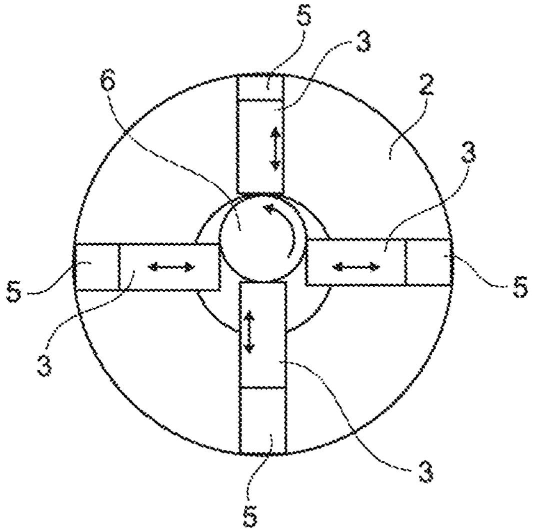
Fig. 2 (Prior art)
FIG. 2 shows a schematic cross-sectional view of a radial piston pump according to the prior art.

One option for providing a force that is to be applied to the upper part 10 or lower part 20 so that a torque about the pivot axis 12 arises consists in the provision of hydraulic fluid via a hydraulic pump. An example of a radial piston pump or a sliding vane rotary pump is depicted in FIG. 2.

Four pistons 3 as displacement elements or driven elements are disposed in a housing 2. The pistons 3 are longitudinally displaceably mounted in cylinder bores within the housing 2 and each form a pump chamber 5, the volume of which is changed when the displacement elements 3 are displaced accordingly. The displacement is caused by a force transmission element 6, which is a cam in the exemplary embodiment of a radial piston pump. The cam 6 revolves in a bore within the housing and causes a radially outward displacement of the pistons when the cam 6 approaches the extent of the bore within the housing. When the cam moves away, the pistons 3 are moved back and the pump chambers 5 become larger. When there is an increase in the pump volume, hydraulic fluid is sucked in, and this is accordingly ejected in the case of a reduction.

Figure 3:
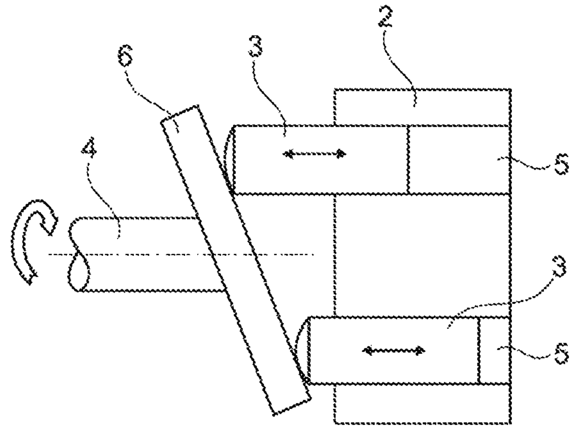
Fig. 3 (Prior art)
FIG. 3 shows a schematic longitudinal section representation of an axial piston pump according to the prior art.

An alternative solution for a hydraulic pump is schematically depicted in FIG. 3. FIG. 3 shows the schematic representation of an axial piston pump with a force transmission element 6 mounted on a driveshaft 4. The displacement element 6 is in the form of a swash plate and is supported on two displacement elements 3 or driven elements, or more displacement elements 3, within the pump housing 2. Depending on the position of the swash plate 6, the piston 3 is pushed into the housing 2 in order to reduce the size of the pump chamber 5, or facilitates a reverse movement out of the housing 2 in order to increase the size of the pump chamber 5.

In both pump types, the hydraulic fluid is conveyed as a result of the oscillations of the pistons 3 as displacement elements. The diameter and the stroke of the piston 3 or of the pistons 3 together with the rotational speed determine the volumetric flow rate. The stroke is dependent on the eccentricity of the cam as force transmission element 6 in the case of radial piston pumps and dependent on the inclination of the swash plate as force transmission element 6 in the case of axial piston pumps.

Figure 4:
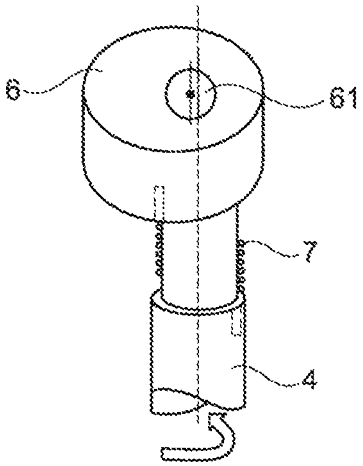
FIG. 4 shows a schematic, perspective representation of a load-dependently adjustable cam.

FIG. 4 shows a partial illustration of a radial piston pump. The basic design corresponds to that of FIG. 2, with the embodiment of the force transmission element 6 in the form of the cam 6 having been modified in relation to the structure in FIG. 2. According to FIG. 4, the force transmission element is in the form of a double cam which has a shaft cam 61, with the cam 6 being able to rotate in relation thereto. The cam 6 is mounted on the driveshaft 4 so as to be rotatable around the shaft cam 61, with the cam 6 as force transmission element being held in an initial position by way of a spring 7. By way of example, if the driveshaft 4 is driven by an electric motor 14, the cam 6 would completely abut against the wall of the bore within the housing 2 and maximally displace the pistons 3 radially to the outside in the case of a lack of counter pressure. However, if the counter pressure in the respective pump chambers 5 increases, there simultaneously is an increase in the resistance to a displacement as a result of the cam 6. This leads to the cam 6 being rotated around the shaft cam 61 counter to the spring force by the spring element 7. As a result, the cam 6 is rotated such that it has reduced eccentricity, as a result of which the volumetric flow rate provided by the displacement element 3 is reduced for an unchanged rotational speed. The higher the resistance or the counter pressure in the hydraulic system, the higher the resistance to a displacement of the pistons 3, and so there is a greater reduction in the eccentricity. Consequently, a load-dependent change in the conveying behavior sets in automatically. In the case of the radial piston pump and the cam arrangement according to FIG. 4, the load-dependent adjustment is implemented by the rotation of the cam 6 in relation to the shaft cam 61 and the changing, effective summated eccentricity which arises on the basis of the angular position of the two cams in relation to one another. The relative angle increases with increasing pressure, resulting in a reduction in the summated eccentricity and a drop in volumetric flow rate.

Figure 5:
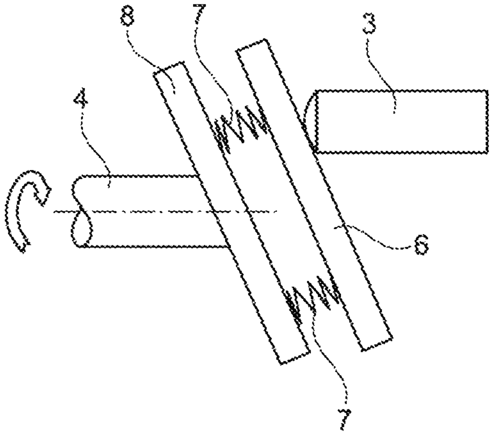
FIG. 5 shows a schematic longitudinal sectional representation of a load-dependently adjustable swash plate.

FIG. 5 shows the load-dependent adjustment, and hence load-dependent adaptation, of the conveyance when maintaining the work point of the electric motor as a result of a resilient mount of the swash plate 6 as force transmission element. The swash plate 6 is mounted by way of a plurality of spring elements 7 on a carrier 8 which is mounted at an angle to the axis of rotation of the driveshaft 4. In the illustrated initial position, the carrier 8 and the swash plate 6 are aligned substantially parallel to one another. If the pressure on the piston 3 increases, for example as a result of an increased hydraulic resistance in the pump chamber (not depicted here), the corresponding spring element 7 is compressed and so the swash plate 6 is displaced in the direction of the carrier 8 that is rigidly fastened to the driveshaft 4. Expressed differently, the piston 3 is displaced with a reduced stroke on account of the resilience of the swash plate 6, leading to a drop in the volumetric flow rate. The higher the resistance, the greater the displacement of the swash plate 6 and the greater the compression of the spring elements 7. In this case, the characteristic of the load-dependent change in the flow rate can be adjusted by changing the elasticities in the spring elements 7. The spring elements 7 can be designed with different levels of stiffness or resilience, they may have a linear, degressive or progressive spring characteristic, or they may also be adjustable in order to retrospectively facilitate an adjustment to the respectively desired behavior of the hydraulic pump.

Figure 6:
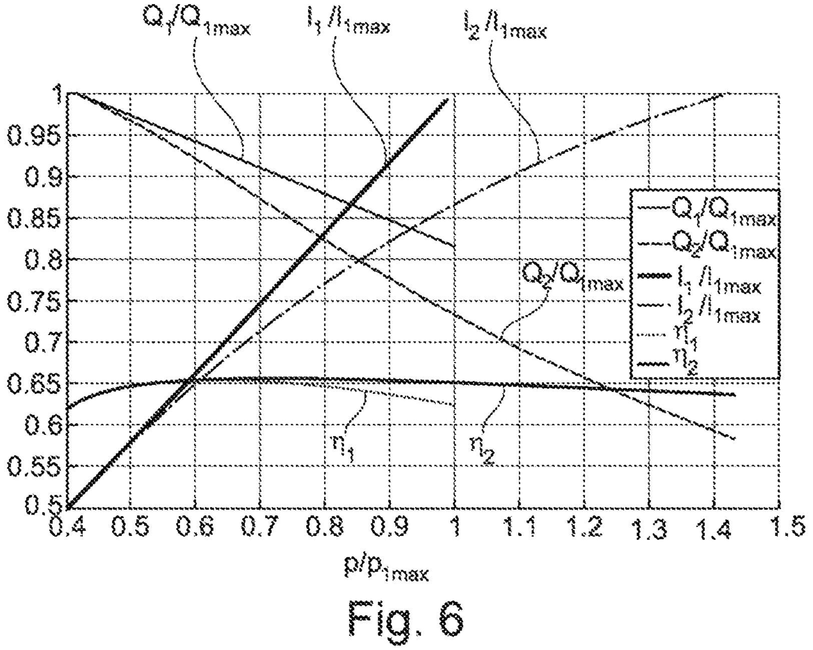
FIG. 6 shows a comparison of characteristics of a radial piston pump with a fixed cam and a load-dependently variable cam.

FIG. 6 plots the behavior of a radial piston pump, once with a fixed eccentricity, denoted by the index 1, and once with a load-dependent, variable eccentricity, represented with the index 2. In this case, the torsional spring 7 was designed such that an increase of the pressure work range to 145% is obtained. What can be gathered from the diagrams is that the admissible maximum current $I_2/I_{1max}$ is only reached at a higher pressure ratio $P/P_{1Max}$ as a result of the work range extension. This results in a steeper drop in the volumetric flow rate $Q_2/Q_{1Max}$ as a function of pressure, as desired for the application. The efficiency $\eta_2$ remains stable over the entire work range.

Figure 7:
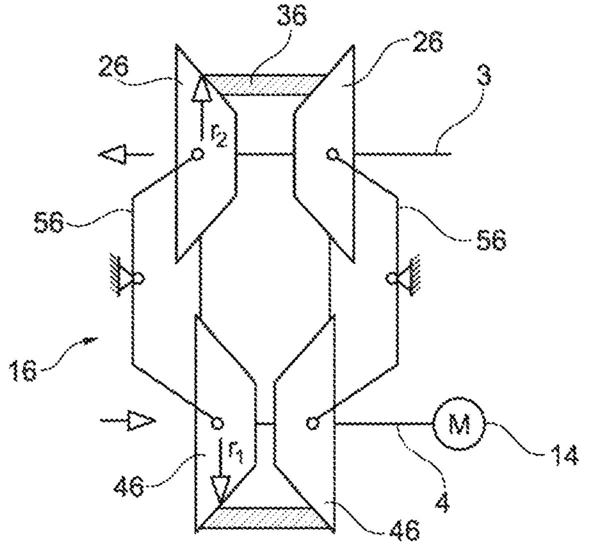
FIG. 7 shows a schematic representation of a continuously variable transmission.

FIG. 7 shows a further variant of the invention, in which the actuator 15 is equipped with a drive 14 and a force transmission device 16 in the form of a continuously variable transmission. An electric motor 14 drives a driveshaft 4, on which two conical pulleys 46 are arranged. The two conical pulleys 46 are mounted in torsionally rigid fashion and mounted so as to be displaceable along the longitudinal extent of the driveshaft 4, for example on a longitudinal gearing. A driven shaft 3 is arranged parallel to the driveshaft 4 and likewise has two conical pulleys 26 displaceably disposed thereon. A belt 36 is disposed between the two conical pulley pairs 26, 46 for the purposes of transmitting the torque from the driveshaft 4 to the driveshaft 3. Alternatively, the conical pulley pairs can be coupled by way of one or more rolling elements. As a result of displacing the respective conical pulleys of a conical pulley pair toward one another or away from one another, there is a change in the respectively active radius $r_1$, $r_2$, resulting in a change in the respective transmission ratio.

Pivotable guide rods 56 are disposed between the two conical pulley pairs 26, 46 and convert a displacement of one conical pulley pair into an opposite movement of the opposite conical pulley pair. The movement of the two conical pulleys toward one another or away from one another can be implemented in load-dependent fashion.

Figure 8:
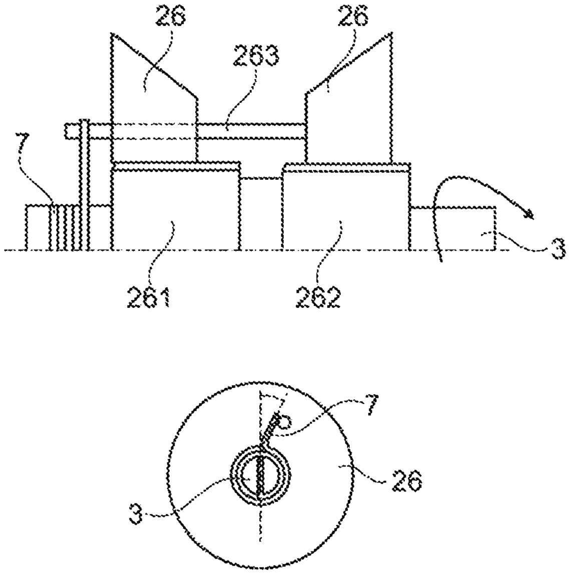
FIG. 8 shows a detailed representation of a load-dependent adjustment mechanism.

An example to this end is depicted in FIG. 8, where the two conical pulleys 26 on the driveshaft 3 are mounted on two oppositely oriented threaded sections 261, 262. Both conical pulleys 26 are coupled in torsionally rigid fashion and are coupled so as to be displaceable relative to one another by way of a guide pin 263 or by way of a plurality of guide pins 263 that are distributed over the circumference. The left conical pulley 26 is prestressed and elastically mounted by way of a torsional spring 7 which is secured firstly to the driven shaft 3 and secondly to one of the conical pulleys 26. By way of example, if there is an increase in the resistance of the driveshaft 3, this leads to a relative rotation of the conical pulleys 26 in relation to the threaded sections 261, 262. The pitch of the threaded sections 261, 262 is chosen in such a way here that the conical pulleys 26 are moved toward one another in the case of an increased resistance. The belt 36 (not depicted here) migrates away from the axis of rotation of the driven shaft 3 on account of the inclination of the conical pulleys 26. On account of the rigid coupling by way of the guide rods 56, the drive-side conical pulleys 46 are moved apart, the belt 36 accordingly migrates closer to the axis of rotation of the driveshaft 4 on account of the same inclination of the conical pulleys 46. There is a change in transmission on account of the changing radii at the conical pulleys, with the driveshaft 3 having a slower rotation in the case of the same rotational speed of the driveshaft 4. As a result, a reduction in the volumetric flow rate can be achieved depending on the resistance present at the driven shaft 3 without leaving the work point of the drive motor 14.

The invention claimed is:

1. An orthopedic joint device having an upper part, a lower part pivotably disposed thereon, and an actuator which is fastened to the upper part and the lower part and which comprises a driveshaft coupled to a driven element by way of a force transmission device, wherein the force transmission device comprises a load-dependently adjustable force transmission element, wherein the actuator comprises a hydraulic pump having a housing and the driven element comprises at least one displacement element, the at least one displacement element being coupled to the driveshaft and being mounted in the housing in a pump chamber, with the load-dependently adjustable force transmission element being disposed between the at least one displacement element and the driveshaft and bringing about a load-dependent change in a stroke of the at least one displacement element.

2. The orthopedic joint device as claimed in claim 1, wherein the load-dependently adjustable force transmission element is mounted elastically.

3. The orthopedic joint device as claimed in claim 1, wherein the at least one displacement element comprises a piston of an axial piston pump and the load-dependently adjustable force transmission element comprises a swash plate, or wherein the at least one displacement element comprises a piston of a radial piston pump and the load-dependently adjustable force transmission element comprises a cam, or wherein the at least one displacement element comprises a rotor of a sliding vane rotary pump and the load-dependently adjustable force transmission element comprises a cam.

4. The orthopedic joint device as claimed in claim 1, further comprising at least one spring element that is compressed during an increasing load and is disposed between the driveshaft and the at least one displacement element.

5. The orthopedic joint device as claimed in claim 4, wherein the at least one spring element comprises an elastomeric spring, coil spring, spiral coil spring, Belleville spring, Belleville spring assembly or leaf spring.

6. The orthopedic joint device as claimed in claim 4, wherein the at least one spring element has a linear, degressive or progressive spring characteristic.

7. The orthopedic joint device as claimed in claim 1, wherein the force transmission device comprises a continuously variable, adjustable transmission.

8. The orthopedic joint device as claimed in claim 7, wherein the load-dependently adjustable force transmission element comprises a conical pulley comprising the driven element on the driveshaft or a driven shaft displaceable along a longitudinal extent of the driveshaft.

9. The orthopedic joint device as claimed in claim 8, wherein the conical pulley is coupled to a spring element which is prestressed against a displacement of the load-dependently adjustable force transmission element.

10. An orthopedic joint device comprising:

an upper part;

a lower part pivotably disposed on the upper part; and an actuator fastened to the upper part and the lower part, the actuator further comprising a hydraulic pump and a driveshaft, the driveshaft being coupled to a driven element by a force transmission device;

wherein the force transmission device comprises a load-dependently adjustable and elastically-mounted force transmission element.

11. The orthopedic joint device of claim 10, wherein the hydraulic pump has a housing and wherein the driven element is coupled to the driveshaft and mounted in the housing in a pump chamber.

12. The orthopedic joint device of claim 11, wherein the driven element comprises a displacement element, and wherein the load-dependently adjustable and elastically-mounted force transmission element is disposed between the driven element and the driveshaft to cause a load-dependent change in a stroke of the displacement element.

13. The orthopedic joint device of claim 12, wherein the displacement element is a piston of an axial piston pump and wherein the load-dependently adjustable and elastically-mounted force transmission element is a swash plate.

14. The orthopedic joint device of claim 12, wherein the displacement element is a piston of a radial piston pump and wherein the load-dependently adjustable and elastically-mounted force transmission element is a cam.

15. The orthopedic joint device of claim 12, wherein the displacement element is a rotor of a sliding vane rotary pump and wherein the load-dependently adjustable and elastically-mounted force transmission element is a cam.

16. The orthopedic joint device of claim 12, further comprising at least one spring element disposed between the driveshaft and the displacement element.

17. The orthopedic joint device as claimed in claim 16, wherein the at least one spring element is an elastomeric spring, coil spring, spiral coil spring, Belleville spring, Belleville spring assembly or leaf spring.

18. An orthopedic joint device comprising:

an upper part;

a lower part pivotably disposed on the upper part; and an actuator fastened to the upper part and the lower part, the actuator further comprising a hydraulic pump and a driveshaft, the driveshaft being coupled to a driven element by a continuously variable, adjustable transmission;

wherein the continuously variable, adjustable transmission comprises a load-dependently adjustable and elastically-mounted conical pulley.

19. The orthopedic joint device of claim 18, wherein the load- dependently adjustable and elastically-mounted conical pulley is coupled to a spring element which is prestressed against a displacement of the continuously variable, adjustable transmission.

* * * * *